United States Patent
Liu (10) Patent No.: US 8,940,959 B2
(45) Date of Patent: *Jan. 27, 2015

(54) DISPOSABLE ABSORBENT ARTICLES HAVING INKJET PRINTED WETNESS INDICATORS

(75) Inventor: Kuang-kai Liu, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 676 days.

This patent is subject to a terminal disclaimer.

(21) Appl. No.: 11/365,006

(22) Filed: Mar. 1, 2006

(65) Prior Publication Data

US 2006/0149198 A1 Jul. 6, 2006

Related U.S. Application Data

(63) Continuation-in-part of application No. 10/827,087, filed on Apr. 19, 2004, now Pat. No. 7,332,642.

(51) Int. Cl.
*A61F 13/42* (2006.01)

(52) U.S. Cl.
CPC ........... *A61F 13/42* (2013.01); *A61F 2013/422* (2013.01)
USPC ....................................................... 604/361

(58) Field of Classification Search
CPC .............. A61F 13/42; A61F 2013/422; A61F 2013/426
USPC ............................. 604/358, 361, 362, 385.01
See application file for complete search history.

(56) References Cited

U.S. PATENT DOCUMENTS

| | | | |
|---|---|---|---|
| 3,675,654 A | | 7/1972 | Baker et al. |
| 4,022,211 A | | 5/1977 | Timmons et al. |
| 4,192,311 A | * | 3/1980 | Felfoldi ................ 604/361 |
| 4,738,674 A | | 4/1988 | Todd et al. |
| 4,744,113 A | | 5/1988 | Kogut |
| 4,909,879 A | | 3/1990 | Ball |
| 4,999,646 A | * | 3/1991 | Trask .................. 347/41 |
| 5,197,958 A | | 3/1993 | Howell |
| 5,354,289 A | | 10/1994 | Mitchell et al. |

(Continued)

FOREIGN PATENT DOCUMENTS

| | | |
|---|---|---|
| BR | 0105879-7 A | 7/2002 |
| EP | 0 776 645 A | 6/1997 |

(Continued)

OTHER PUBLICATIONS

U.S. Appl. No. 11/365,000, filed Mar. 1, 2006, All Office Actions and Responses beginning Sep. 24, 2008.

*Primary Examiner* — Melanie Hand
*Assistant Examiner* — Paula L Craig
(74) *Attorney, Agent, or Firm* — Kathleen Y. Carter; William E. Gallagher; Andrew A Paul (57) ABSTRACT

The present invention relates to disposable absorbent articles. The disposable absorbent articles include: (a) a body contacting surface; (b) a garment contacting surface opposite the body contacting surface; and (c) an inkjet printed wetness indicator which is seen through either the body contacting surface or the garment contacting surface. The wetness indicator includes a central graphic and a background graphic, the central graphic having at least one permanent ink composition and the background graphic having at least one water soluble ink composition.

17 Claims, 3 Drawing Sheets

(56) References Cited

U.S. PATENT DOCUMENTS

| | | | |
|---|---|---|---|
| 5,389,093 A | 2/1995 | Howell | |
| 5,458,590 A | 10/1995 | Schleinz et al. | |
| 5,595,754 A | 1/1997 | Ito et al. | |
| 5,690,624 A | 11/1997 | Sasaki et al. | |
| 5,743,946 A * | 4/1998 | Aoki et al. | 106/31.95 |
| 5,766,212 A | 6/1998 | Jitoe et al. | |
| 5,766,389 A * | 6/1998 | Brandon et al. | 156/64 |
| 5,834,099 A | 11/1998 | Steinhardt et al. | |
| 5,902,669 A | 5/1999 | Steinhardt et al. | |
| 5,947,943 A | 9/1999 | Lee | |
| 5,965,485 A * | 10/1999 | Mizumachi et al. | 503/227 |
| 6,075,178 A | 6/2000 | La Wilhelm et al. | |
| 6,297,424 B1 * | 10/2001 | Olson et al. | 604/361 |
| 6,307,119 B1 | 10/2001 | Cammarota et al. | |
| 6,596,918 B1 * | 7/2003 | Wehrle et al. | 604/361 |
| 6,710,221 B1 | 3/2004 | Pierce et al. | |
| 7,332,642 B2 | 2/2008 | Liu | |
| 8,348,920 B2 * | 1/2013 | Liu | 604/391 |
| 8,568,384 B2 * | 10/2013 | Liu | 604/391 |
| 2001/0049513 A1 * | 12/2001 | Neading et al. | 604/361 |
| 2003/0073966 A1 * | 4/2003 | Sosalla et al. | 604/361 |
| 2003/0164136 A1 | 9/2003 | Klofta et al. | |
| 2004/0064113 A1 | 4/2004 | Erdman et al. | |
| 2004/0233241 A1 * | 11/2004 | Salacz | 347/12 |
| 2005/0043438 A1 * | 2/2005 | Moore et al. | 523/160 |
| 2005/0234415 A1 * | 10/2005 | Liu | 604/361 |

FOREIGN PATENT DOCUMENTS

| | | | |
|---|---|---|---|
| EP | 0818569 A2 | | 1/1998 |
| EP | 1 222 907 A2 | | 7/2002 |
| GB | 2 177 977 A | | 2/1987 |
| GB | 2 327 354 A | | 1/1999 |
| GB | 2 336 112 A | | 10/1999 |
| JP | 59-024704 U | * | 2/1984 |
| JP | 60-20509 U | | 2/1985 |
| JP | 60-020509 U | * | 2/1985 |
| JP | 61-137606 U | | 8/1986 |
| JP | 1-250843 | | 10/1989 |
| JP | 3-221039 A | | 9/1991 |
| JP | 4-15999 U | | 2/1992 |
| JP | 11-004852 A | | 1/1999 |
| JP | 13-327530 A | | 11/2001 |
| JP | 14-2823014 A | | 10/2002 |
| JP | 2004-049405 | | 2/2004 |
| JP | 2004-049405 A | | 2/2004 |
| WO | WO 95/00099 A1 | | 1/1995 |
| WO | WO 00/76438 A2 | | 12/2000 |
| WO | WO 00/76442 A1 | | 12/2000 |
| WO | WO 00/76558 A1 | | 12/2000 |
| WO | WO 01/41691 A1 | | 6/2001 |

* cited by examiner

DISPOSABLE ABSORBENT ARTICLES HAVING INKJET PRINTED WETNESS INDICATORS

CROSS REFERENCE TO RELATED APPLICATION

This is a continuation-in-part of application Ser. No. 10/827,087 filed on Apr. 19, 2004 now U.S. Pat. No. 7,332,642.

FIELD OF THE INVENTION

The present invention relates generally to disposable absorbent articles. The present invention also relates to disposable absorbent articles containing inkjet printed wetness indicators. Another aspect of the present invention, relates to methods of printing wetness indicators onto disposable absorbent articles.

BACKGROUND OF THE INVENTION

Infants and other incontinent individuals wear a disposable article such as a disposable diaper to receive and contain urine and other body exudates. Absorbent articles function to contain the discharged materials and to isolate these materials from the body of the wearer and from the wearer's garments and bed clothing. It is generally known in the art that disposable absorbent articles have many different basic designs. Examples of such disposable articles include disposable diapers (for baby and adult) including pull-on diapers and training pants, disposable absorbent pads including sanitary napkins, pantiliners and incontinent pads, disposable underwears, and disposable panties for menstrual use.

The exterior of these disposable absorbent articles is covered with a flexible, liquid impervious member to prevent leakage of absorbed liquids from the disposable absorbent articles. Such a liquid impervious member is generally referred to as a backsheet, and is often constructed from a liquid impervious material such as a polyethylene film, and other outer cover material such as a nonwoven material (if desired). The backsheet constitutes the garment contacting surface of the absorbent articles.

More often than not disposable absorbent articles are incorporating graphics as an ordinary feature. In most instances, these graphics are applied to the backsheet of the product so that the graphics are visible while the product is being worn. The graphics have been printed directly on a component of the backsheet or have been printed on a separate layer, such as a tissue or nonwoven web layer, which is disposed on the backsheet.

There are many reasons to incorporate graphics in disposable absorbent articles. For instance, the graphics can improve the appearance and appeal of the product, to both the wearer and the purchaser. Graphics can also impact the manner in which a disposable absorbent article is used. For example, graphics on disposable diapers can be used by caregivers to amuse and/or educate a child during diapering. Similarly, graphics on disposable training pants can provide educational and motivational mechanisms to facilitate the toilet training process. Graphics on training pants can also serve to increase the child's interest in the product and thereby increase the child's interest in the toilet training process.

Graphics can further be used to indicate when a urine insult has occurred. For instance, it has been known in the art that upon wetting, disposable absorbent articles like diapers have included graphics that appear or disappear to indicate the insult.

Those graphics are typically printed by using conventional printing techniques such as the gravure and flexography technologies which employ a printing plate to print the graphic on the backsheet. The printing plate has ink images for graphics to be printed. The printing plate is typically mounted on a printing cylinder in a printing process. In the printing process, when the cylinder rotates, the printing plate contacts the backsheet to transfer the ink images to the backsheet thereby printing the graphics thereon.

The number of the ink images which can be prepared in the printing plate depends on the sizes of the ink images (or the graphics to be printed), the printing plate and the cylinder. In general, since the size of the backsheet is relatively large, the size of the repeated ink images tends to be large. This means that the total area of the printing plate is occupied by a small number of ink images. As a result, the number of the graphics to be printed is limited in particular for a relatively large component material of disposable absorbent articles such as a backsheet material.

Because of the above reasons, the variety of the graphics printed on conventional disposable absorbent articles within one consumer purchased package is limited. Thus, it is understood that this limitation results in preventing users or consumers from enjoying more variety of graphics in the disposable absorbent articles packed or contained in one package. Further, this limitation has become a restriction in illustrating a complete theme which is typically believed to be helpful to children's education or development.

Consequently, disposable absorbent products which include an unlimited number of graphics that can change appearances upon exposure to liquid are desirable.

SUMMARY OF THE INVENTION

In one embodiment, the present invention is directed to disposable absorbent articles. The disposable absorbent articles include: (a) a body contacting surface; (b) a garment contacting surface opposite the body contacting surface; and (c) an inkjet printed wetness indicator which is seen through either the body contacting surface or the garment contacting surface. The wetness indicator includes a central graphic and a background graphic, the central graphic having at least one permanent ink composition and the background graphic having at least one water soluble ink composition.

In another embodiment, the present invention is directed to disposable absorbent articles. The disposable absorbent articles include: (a) a liquid pervious topsheet; (b) a liquid impervious backsheet that is at least partially joined to the topsheet; (c) an absorbent core disposed at least partially between the topsheet and the backsheet; and (d) a wetness indicator inkjet printed onto a surface of either the absorbent core or the backsheet, the wetness indicator having a central graphic and a background graphic. The central graphic includes at least one permanent ink composition and the background graphic includes at least one water soluble ink composition.

In yet another embodiment, the present invention is directed to a method of printing a wetness indicator onto an absorbent article. The method includes the steps of: A method of printing a wetness indicator onto an absorbent article, the method comprising the steps of: (a) providing an absorbent article wherein said article comprises a topsheet, a backsheet and an absorbent core; and (b) inkjet printing a wetness indicator onto a surface of the absorbent article. The wetness indicator includes a central graphic and a background graphic, wherein the central graphic includes at least one permanent ink composition and the background graphic includes at least one water soluble ink composition.

BRIEF DESCRIPTION OF THE DRAWINGS

While the specification concludes with claims which particularly point out and distinctly claim the invention, it is believed the present invention will be better understood from the following description taken in conjunction with the accompanying drawings.

DETAILED DESCRIPTION OF THE INVENTION

All documents cited in the Detailed Description of the Invention are, in relevant part, incorporated herein by reference; the citation of any document is not to be construed as an admission that it is prior art with respect to the present invention.

As used herein, the term "absorbent articles" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "body contacting surface" refers to the surface of absorbent articles which primarily contacts the body of the wearer, while "garment contacting surface" refers to the surface of the absorbent articles that primarily contacts the wearer's garment when the absorbent articles are worn. Typically, the body contacting surface is the body facing surface of a topsheet, while the garment contacting surface is the garment facing surface of a backsheet.

As used herein, the term "bonded" refers to different materials being attached (cohesively or adhesively) in at least a portion thereof. The attached portions may be random or may have a pattern such as stripes, spirals, dots, and the like. The attached portions may be located at the peripheries, throughout the surface area, or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "composite structure" refers to a multi-region structure wherein the materials comprising the regions may be operatively associated or bonded. The regions may even be in intimate contact such that the composite has a unitary structure. Further, the regions may be positioned in a layered (face-to-face) arrangement, or a side-by-side arrangement.

As used herein, the term "disposable" is used in its ordinary sense to mean an article that is disposed or discarded after a limited number of usage events over varying lengths of time, preferably less than about 20 events, more preferably less than about 10 events, even more preferably less than about 5 events, and most preferably less than about 2 events.

As used herein, "graphic" refers to images or designs that are constituted by a figure (i.e., a line(s)), a symbol or character, a color difference or transition of at least two colors, or the like. The graphic may have has an aesthetic image or design that can provide certain benefit(s) when the absorbent article of the invention is looked or viewed by users or consumers. A variety of graphics can be used in the absorbent articles of the invention. Such graphics will be described in detail hereinafter.

As used herein, the term "intimate bonding" refers to physical contact between two layers such that they resist separation with no readily visually identifiable areas of separation. In one particular embodiment, the inner and outer layers are adhesively laminated together in the graphic regions using a meltblowing process to form an overlapping network of adhesive filaments.

As used herein, the term "joined" encompasses configurations wherein an element is directly secured to the other element by affixing the element directly to the other element, and configurations wherein the element is indirectly secured to the other element by affixing the element to intermediate member(s), which in turn are affixed to the other element.

The term "macroporous" refers to materials having pores too large to effect capillary transport of fluid, generally having pores greater than about 0.5 mm in diameter and, more specifically, having pores greater than about 1.0 mm in diameter.

As used herein, the terms "meltblown" and "meltblown web" refer to a web having fibers formed by extruding a molten thermoplastic material through a plurality of fine, usually circular, die capillaries as molten threads or filaments into converging high velocity heated gas/air streams which attenuate the molten filaments to reduce their diameter. The reduction in fiber diameter is substantially greater then the reduction of fiber diameter in the spunbonding process, resulting in microfibers having average fiber diameter larger than 0.2 microns and typically in the range of 0.6 to 10 microns. Thereafter, the meltblown fibers are carried by the high velocity gas stream and are deposited on a collecting surface to form a web of randomly disbursed fibers. Various meltblown processes are known in the art.

As used herein, the term "microporous" refers to materials which are capable of transporting fluids by capillary action.

As used herein, the terms "nonwoven" and "nonwoven web" refers to a web that has a structure of individual fibers which are interlaid forming a matrix, but not in an identifiable repeating manner. Nonwoven webs may be formed by a variety of processes known to those skilled in the art, for example, meltblowing, spunbonding, wet-laying, air-laying, and various bonding-carding processes.

As used herein, the term "operatively associated" refers to a structure comprising different materials positioned at least in partial contact with each other in use. The materials are physically separable and each exhibits properties that can be measured individually. The materials may be arranged in a face-to-face relationship in the z-dimension, or in a side-by-side relationship in the xy-dimension.

As used herein, the term "pulp" or "cellulosic fibers" include those natural fiber derived from trees or vegetations (e.g., hardwood fibers, softwood fibers, hemp, cotton, flax, esparto grass, milkweed, straw, bagasse and the like), their processed/regenerated fibers (e.g., Rayon®) or chemically derivatized fibers (e.g., cellulose esters), and combinations thereof. Suitable hardwood fibers include eucalyptus fibers. Suitable hardwood fibers may be prepared by kraft or other chemical pulping methods. Suitable softwood fibers include southern softwood (SS) fibers and northern softwood (NS) fibers. Softwood fibers for use herein can be chemically (e.g., without limitation, kraft pulp) or mechanically pulped (e.g., without limitation, chemithermal mechanical pulp (CTMP) and thermal mechanical pulp (TMP)).

As used herein, the term "region" refers to a zone or an area comprising a material being physically, chemically, or visually distinguishable from surrounding or adjoining materials. Various regions of materials may include transitional regions in between. The regions may be positioned in the z-dimension or in the xy-dimension. As used herein, the term "z-dimension" refers to the dimension orthogonal to the length and width of the structure or article. The z-dimension usually corresponds to the thickness of the structure or article. As used herein, the term "xy-dimension" refers to the plane orthogonal to the thickness of the member, core or article when the member, core or article is in a flat-out state. The xy-dimension usually corresponds to the length and width, respectively, of the structure or article in a flat-out state.

As used herein, the terms "spunbond" and "spunbonded web" refers to a web having fibers formed by extruding a molten thermoplastic material as filaments from a plurality of fine capillaries of a spinnerette having a circular or other configuration, then rapidly reducing the diameter of the extruded filaments by fluid drawing or other well known spunbonding mechanisms. Spunbond fibers are quenched and generally not tacky when they are deposited onto a collecting surface. Spunbond fibers are generally continuous and often have average between about 10 to about 30 microns.

As used herein, the term "unitary structure" refers to a structure comprising materials having different characteristics joined together to form an integral entity such that the materials are substantially inseparable physically, and the unitary structure exhibits properties resulting from the combination of the materials therein. The materials may be arranged in a face-to-face relationship in the z-dimension, or in a side-by-side relationship in the xy-dimension.

Absorbent Article

Figure 1:
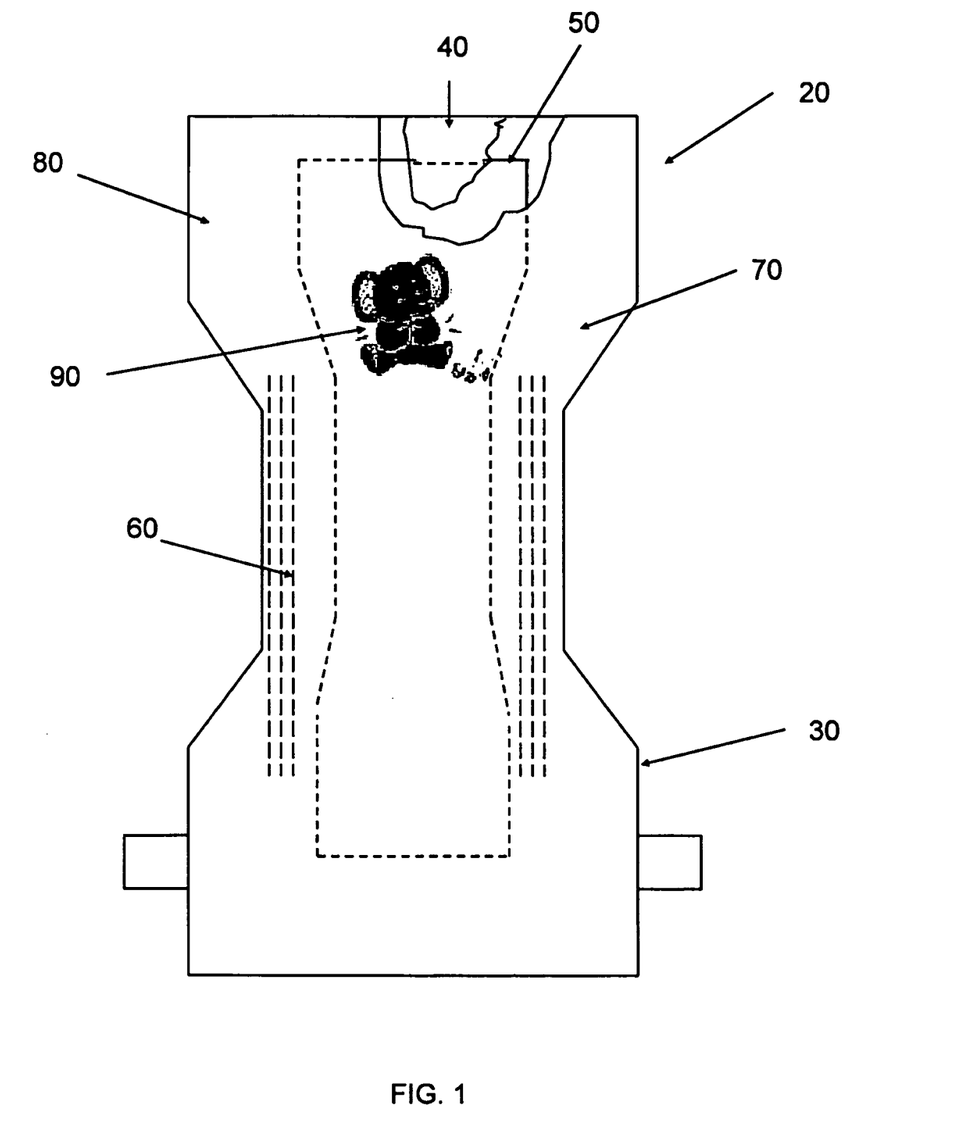
FIG. 1 illustrates a partially cut-away plan view of an absorbent article in accordance with one embodiment of the present invention, which is viewed from the garment contacting surface.

FIG. 1 is a partially cut-away plan view of an absorbent article, for example, a diaper 20 (as one example of absorbent articles). In one embodiment, as further shown, the diaper 20 includes a plurality of component materials, for example, a backsheet 30, a topsheet 40, an acquisition layer (not shown), an absorbent core 50 and a barrier leg cuff material 60, disposed between the body contacting surface (not shown) and the garment contacting surface 70. The outermost surface of the backsheet 30 forms the garment contacting surface 70 of the diaper 20, while the innermost surface of the topsheet 40 forms the body contacting surface (not shown) of the diaper 20.

An outer cover forms the chassis, onto which other components of the diaper are added to form the unitary structure of the diaper. In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, and U.S. Patent Publication 2003/0233082A1.

In certain embodiments, the absorbent articles may additionally include one or more components selected from the group consisting of an outer cover, side panels 80, a cuff, an elastic feature, a fastening system, and combinations thereof.

Topsheet

The absorbent articles of the present invention comprise a topsheet 40. In one example, the topsheet 40 is compliant, soft feeling, and non-irritating to the wearer's skin. It can be elastically stretchable in one or two directions. Further, the topsheet 40 is liquid pervious, permitting liquids (e.g., menses, urine, and/or runny feces) to readily penetrate through its thickness. A suitable topsheet 40 can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet 40 includes fibers, the fibers may be spunbond, carded, wet-laid, meltblown, hydroentangled, or otherwise processed as is known in the art. One suitable topsheet comprising a web of staple-length polypropylene fibers is manufactured by Veratec, Inc., a Division of International Paper Company, of Walpole, Mass., under the designation P-8.

In one example, topsheet 40 for use in the present invention is selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. Nos. 5,628,097, 5,916,661, 6,545,197, 6,107,539, and PCT Patent Publication WO 00/69382 A2.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414, 215, 5,342,338, and 5,941,864 and U.S. Patent Publication 2002/017376. In another embodiment of feces handling articles, such topsheets can be combined with feces handling members, e.g. underlying such topsheets, and which are further described in the abovementioned patent documents.

Suitable formed film topsheets are described in U.S. Pat. Nos. 3,929,135, 4,324,246, 4,342,314, 4,463,045, 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T."

In one embodiment, at least a portion of the topsheet 40 is made of a hydrophobic material or is treated to be hydrophobic in order to isolate the wearer's skin from liquids contained in the absorbent core. If the topsheet 40 is made of a hydrophobic material, preferably at least a portion of the upper surface of the topsheet 40 is treated to be hydrophilic so that liquids will transfer through the topsheet 40 more rapidly. The topsheet 40 can be rendered hydrophilic by treating it with a surfactant or by incorporating a surfactant into the topsheet. Suitable methods for treating the topsheet 40 with a surfactant include spraying the topsheet material with the surfactant and/or immersing the material into the surfactant. A more detailed discussion of such a treatment and hydrophilicity is contained in U.S. Pat. Nos. 4,988,344, 4,988,345, and 4,950,254. A more detailed discussion of some suitable methods for incorporating a surfactant in the topsheet 40 can be found in U.S. Statutory Invention Registration No. H1670. Alternatively, the topsheet 40 may include an apertured web or film which is hydrophobic. This may be accomplished by eliminating the hydrophilizing treatment step from the production process and/or applying a hydrophobic treatment to the topsheet 40, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 40 may be coated with a lotion as is known in the art. Examples of suitable lotions include those described in U.S. Pat. Nos. 5,607,760, 5,609,587, 5,635,191, 5,643,588, and 5,968,025. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet 40 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 cm$^2$ and about 50 cm$^2$. The aperture preferably has an area of between about 15 cm$^2$ and 35 cm$^2$.

Further, the topsheet 40 may be fully or partially elasticated or may be foreshortened so as to provide a void space between the topsheet and the core. Exemplary structures including elasticized or foreshortened topsheets are described in more detail in U.S. Pat. Nos. 4,892,536, 4,990,147, 5,037,416, and 5,269,775.

Backsheet

In one embodiment, the backsheet 30 is impervious to fluids (e.g., menses, urine, and/or runny feces) and is manufactured from a thin plastic film, although other flexible liquid impervious materials may also be used. As used herein, the term "flexible" refers to materials which are compliant and will readily conform to the general shape and contours of the human body. The backsheet 30 prevents the exudates absorbed and contained in the absorbent core from wetting articles which contact the absorbent article such as bedsheets, pants, pajamas and undergarments. The backsheet 30 may thus comprise a woven or nonwoven material, polymeric films such as thermoplastic films of polyethylene or polypropylene, and/or composite materials such as a film-coated nonwoven material (i.e., having an inner film layer and an outer nonwoven layer). A suitable backsheet is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet is preferably embossed and/or matte-finished to provide a more clothlike appearance. Further, the backsheet 30 may permit vapors to escape from the absorbent core (i.e., the backsheet is breathable) while still preventing exudates from passing through the backsheet. The size of the backsheet 30 is dictated by the size of the absorbent core 50 and the exact absorbent article design selected.

The backsheet 30 and the topsheet 40 are positioned adjacent a garment surface and a body surface, respectively, of the absorbent core 50. In one embodiment, the absorbent core 50 is joined with the topsheet 40, the backsheet 30, or both in any manner as is known by attachment means such as those well known in the art. However, embodiments of the present invention are envisioned wherein portions of the entire absorbent core are unattached to one or both of the topsheet 40 and the backsheet 30.

For example, the backsheet 30 and/or the topsheet 40 may be secured to the absorbent core 50 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258, HL-1358, or H-2031. The attachment means will preferably comprise an open pattern network of filaments of adhesive as is disclosed in U.S. Pat. No. 4,573,986. An exemplary attachment means of an open pattern network of filaments comprises several lines of adhesive filaments swirled into a spiral pattern such as illustrated by the apparatus and method shown in U.S. Pat. Nos. 3,911,173, 4,785,996 and 4,842,666. Alternatively, the attachment means may comprise heat bonds, pressure bonds, ultrasonic bonds, dynamic mechanical bonds, or any other suitable attachment means or combinations of these attachment means as are known in the art.

In one embodiment, the backsheet 30 includes an inner and outer layer, each of which can be bonded to the other by a variety of means known in the art, including thermal bonds, adhesive bonds, ultrasonic lamination, or the like. Intimate bonding of the inner and outer layers in the graphic regions reduces light diffraction and thus improves the brightness and overall visibility of the wetness indicator graphic. Adhesive bonding can also be accomplished using adhesive slot coating, high frequency oscillation patterns, for example in swirl or spray patterns, and other fine denier and/or high coverage application techniques. Suitable laminate adhesives, which can be applied continuously or intermittently, can be obtained from Findley Adhesives, Inc. or from National Starch and Chemical Company.

The outer layer of the backsheet 30 can be made in a variety of forms using different processes. For example, the outer layer may be formed as a carded web, a bonded carded web, a spunbond web, a needled fabric, a woven fabric, or the like to provide a generally cloth-like texture to the wearer. Other additives such as titanium dioxide can represent about 0.5% or less, particularly about 0.3% or less, of the outer layer. In one particular embodiment, the outer layer comprises a spunbond web formed of about 99.5 to 100% polypropylene resin and about 0.5% or less other additives. In one embodiment, the outer layer is a lightweight material having a basis weight of about 15 to about 30 gsm and in another embodiment from about 15 to about 25 gsm.

Absorbent Core

The articles of the present invention additionally comprise one or more absorbent cores 50. The absorbent core 50 is at least partially disposed between the topsheet 40 and the backsheet 30 and may take on any size or shape that is compatible with the disposable absorbent article. Exemplary absorbent structures for use as the absorbent core 50 of the present invention that have achieved wide acceptance and commercial success are described in U.S. Pat. Nos. 4,610,678, 4,673, 402, and 4,888,231, and 4,834,735. The absorbent core 50 may further comprise the dual core system containing an acquisition/distribution core of chemically stiffened fibers positioned over an absorbent storage core as detailed in U.S. Pat. Nos. 5,234,423 and 5,147,345.

In general, the absorbent core 50 is capable of absorbing or retaining liquids (e.g., menses, urine, and/or other body exudates). The absorbent core 50 is preferably compressible, conformable, and non-irritating to the wearer's skin. The absorbent core 50 may be manufactured in a wide variety of sizes and shapes (e.g., rectangular, oval, hourglass, "T" shaped, dog bone, asymmetric, etc.). The absorbent core 50 may include any of a wide variety of liquid-absorbent materials commonly used in absorbent articles, such as comminuted wood pulp, which is generally referred to as airfelt. Examples of other suitable absorbent materials for use in the absorbent core 50 include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5,260,345. The configuration and construction of the absorbent core 50 may also be varied (e.g., the absorbent core may have varying caliper zones and/or have a profile so as to be thicker in the center; hydrophilic gradients; superabsorbent gradients; or lower average density and lower average basis weight zones, e.g., acquisition zones; or may comprise one or more layers or structures). The total absorbent capacity of the absorbent core 50 should, however, be compatible with the design loading and the intended use of the absorbent article. Further, the size and absorbent capacity of the absorbent core 50 may be varied to accommodate different uses such as diapers, incontinence pads, pantiliners, regular sanitary napkins, and overnight sanitary napkins, and to accommodate wearers ranging from infants to adults. The absorbent core 50 can include other absorbent components that are often used in absorbent articles, for example, a dusting layer, a wicking or acquisition layer, or a secondary topsheet for increasing the wearer's comfort.

In certain embodiments of the present invention, the absorbent article may also include a sublayer disposed between the topsheet 40 and the backsheet 30. The sublayer may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macroporous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Additionally, suitable absorbent cores may contain reduced amounts of cellulosic airfelt material. For instance, such cores may comprise less than about 40%, 30%, 20%, 10%, 5%, or even 1%. Such a core comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335, 5,562, 646, 5,669,894, 6,790,798, US Patent Publications 2004/0158212A1, 2004/0097895A1, U.S. application Ser. Nos. 10/758,375, and 10/758,138, both filed on Jan. 15, 2004.

In further embodiments, the articles of the present invention may further comprise a wetness sensation member. This member may be disposed in various locations within the article. For instance, the wetness sensation member may be disposed on the topsheet. The member may comprise a permeable layer and an impermeable layer, wherein urine passes through the permeable layer and not through the impermeable layer such that a wearer is made of aware of the fact that urination has occurred as a result of the "wet" feeling. Suitable members are detailed in U.S. Pat. No. 6,627,786.

Wetness Indicator

The disposable absorbent articles of the present invention further comprise a wetness indicator 90. The wetness indicator can be located on or against any surface of a component material, including the body contacting surface and the garment contacting surface provided that the wetness indicator 90 remains visible from the exterior of the absorbent article. Non-limiting examples of the component material include the backsheet 30, the topsheet 40, the acquisition layer, the absorbent core 50 and the barrier leg cuffs 60. In another embodiment, the wetness indicator 90 is disposed between the absorbent core 50 and the backsheet 30 and in liquid communication with the absorbent core 50.

Figure 2:
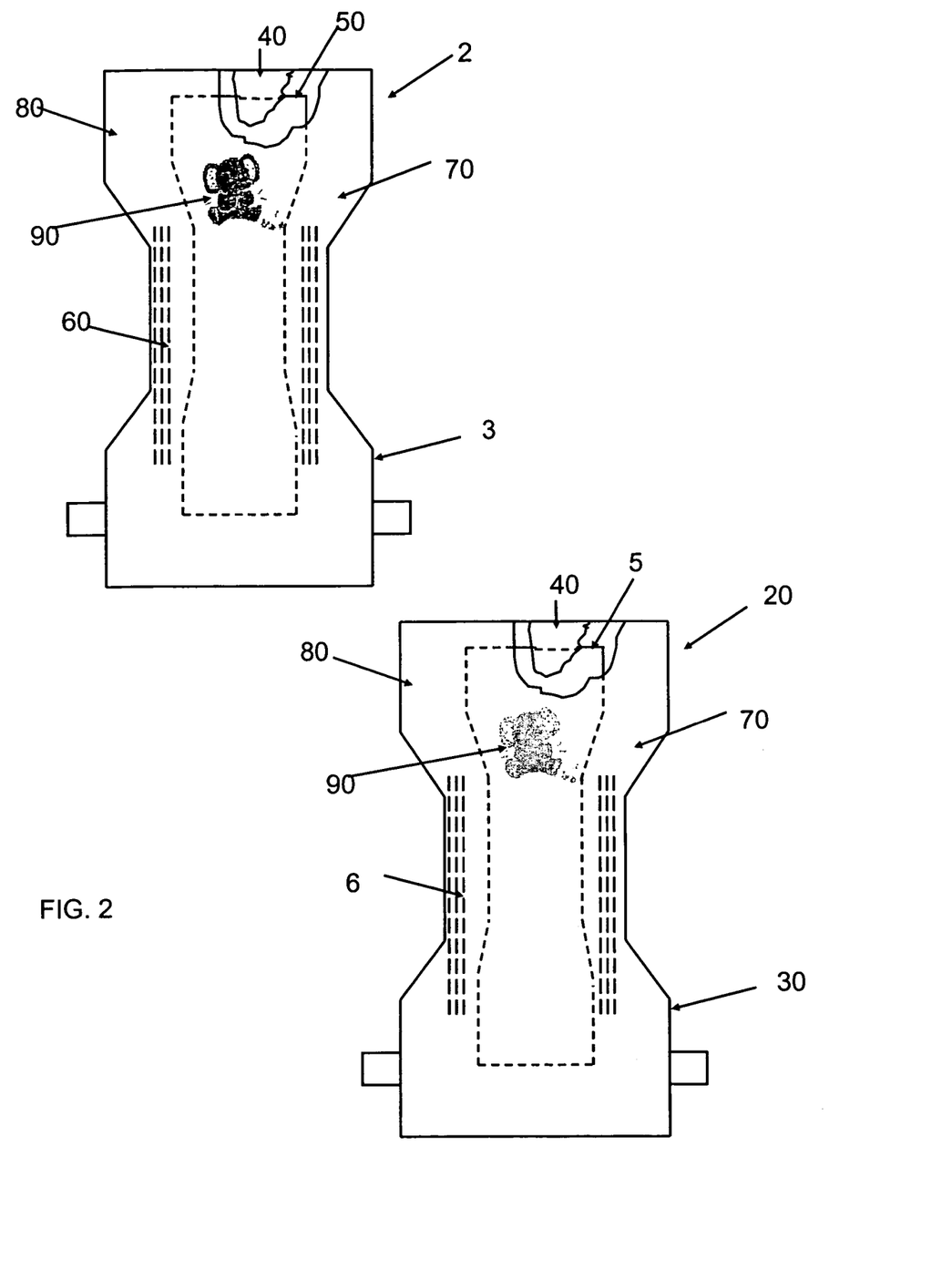
FIG. 2 illustrates a wetness indicator in accordance with one embodiment of the present invention that changes color upon wetting.
Figure 3:
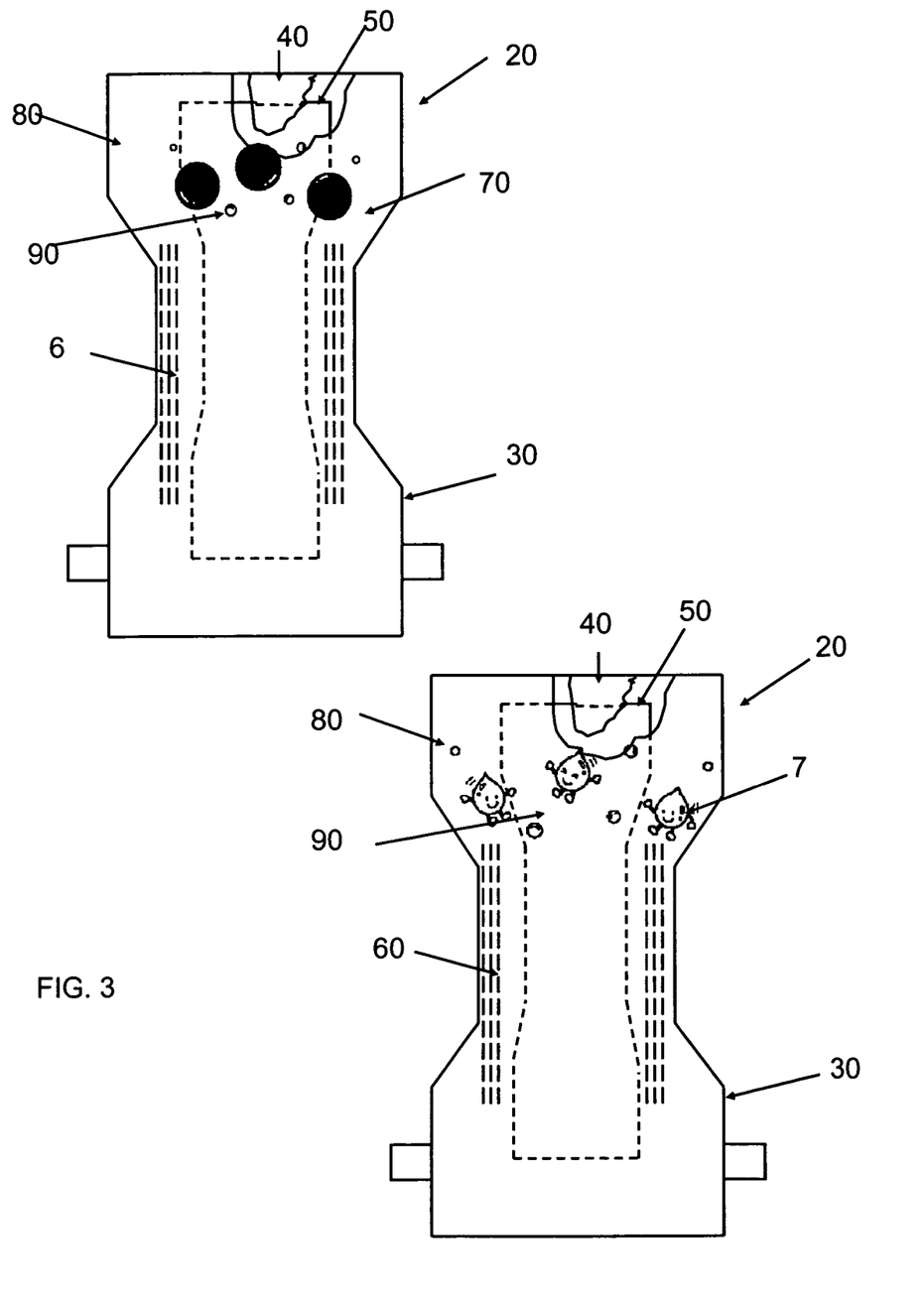
FIG. 3 illustrates a wetness indicator in accordance with one embodiment of the present invention, wherein the background graphic is a series of large and small bubbles that upon wetting becomes a series of raindrops and small bubbles.

The wetness indicator 90 comprises a central graphic and a background graphic that, upon wetting, the wetness indicator 90 exhibits a visible change that is selected from the group consisting of a color change, a graphic change, and combinations thereof. The central graphic includes at least one permanent ink composition and the background graphic includes at least one water soluble ink composition. In certain embodiments, the central graphic is hidden by the background graphic until such time as the graphic is wetted. For instance, FIG. 2 illustrates a background graphic of a colored bear that once wetted reveals a central graphic of a different colored bear. FIG. 3 depicts a central graphic of colored raindrops that are revealed upon wetting of a colored larger animated bubbles background graphic. In still other embodiments, the background graphic may be a different color than the central graphic that is revealed upon wetting. For instance, each of the larger and smaller bubbles in FIG. 3 prior to wetting may be blue in color but after wetting only the smaller sized bubbles may change to pink in color while the raindrops within the larger bubbles may appear pink in color while the surrounding larger bubble remains blue in color after wetting. Alternatively, prior to wetting each of the bubbles may be blue in color and upon wetting the raindrops that are revealed may each be a different color from the original blue bubbles and may still be different colors from one another. In still other embodiments, the background graphic may be an entirely different shape and/or color from the central graphic that appears upon wetting of the graphic.

The central graphic of the present invention includes at least one permanent ink composition. In one embodiment, the permanent ink composition comprises from about 30% to about 90%, by weight of the composition, of an organic solvent, from about 1% to about 10%, by weight of the composition, of a fluid dyestuff, from about 1% to about 10%, by weight of the composition, of a resin, and from about 1% to about 10%, by weight of the composition, of a plasticizer.

Suitable organic solvents include ketones such as acetone, diethyl ketone, cyclophexanone and the likes. Alcohols such as methanol, ethanol, n-propanol, isopropanol, n-butanol, 1-methoxy-2-propanol, and the likes. Esters such as ethyl acetate, propyl acetate, butyl acetate and the likes. Ethers, lactones and amides may also be sued. If desired a mixture of solvents may be used. For example, a small amount of ethanol may be added to methyl ethyl ketone solvent. The organic solvents of the present invention comprise no more than about 50% water, or alternatively, no more than about 30%, 20%, or 10% water.

Suitable fluid dyestuffs include the yellow dyes such as C.I. Solvent Yellow 19 (C.I. 13900A), C.I. Solvent Yellow 21 (C.I. 18690), C.I. Solvent Yellow 80, FD&C Yellow #5, Yellow Shade 16948, Acid Yellow 23 and the like; orange dyes such as C.I. Solvent Orange 1 (C.I. 11920), C.I. Orange 37, C.I. Orange 40 and the like; red dyes such as C.I. Solvent Red 8, C.I. Solvent Red 81, C.I. Solvent Red 82, C.I. Solvent Red 84, C.I. Solvent Red 100 and the like; violet dyes such as C.I. Solvent Violet 8, C.I. Solvent Violet 21 and the like; blue dyes such as C.I. Solvent Blue 2, C.I. Solvent Blue 11, C.I. Solvent Blue 25, C.I. Solvent Blue 36, C.I. Solvent Blue 55 and the like; black dyes such as C.I. Solvent Black 3, C.I. Solvent Black 5, C.I. Solvent Black 7, C.I. Solvent Black 22, C.I. Solvent Black 27, and C.I. Solvent black 29.

Suitable resins include ketone resins, aldehyde resins, cellulous derivative resins, acrylic resinsphenolic resins, rosin resins. Examples of suitable resins include KRUMBHAAR K-1717HMP, KRUMBHAAR K-3107, from Lawter International, Inc. Nitrocellulous 18/28 cP grade from Hercules, Inc.

The type of plasticizer selected should be compatible with the additional resin selected. Suitable plasticizers include diisobutyl adipate, di-n-hexyl adipate and the likes for cellulous nitrate resin. Other examples of plasticizers that will be compatible with cellulous nitrate can be found, e.g., in *Kirk-Othmer—Encyclopedia of Chemical Technology*, vol 18, p. 111-183, 3rd edition.

Exemplary permanent ink compositions that can be used in accordance with the present invention are commercially available from Videojet Technologies, Ill., USA, under the trade names "16-71" and "16-44".

The background graphic of the present invention includes at least one water soluble ink composition. In one embodiment, the water soluble ink composition comprises from about 50% to about 90%, by weight of the composition, of an organic solvent, from about 1% to about 10%, by weight of the composition, of a fluid dyestuff, from about 1% to about 10%, by weight of the composition, of a resin, and from about 1% to about 10%, by weight of the composition, of a plasticizer.

Suitable organic solvents may be selected from the group consisting of alcohols, ketones, esters, ethers amides, lactones, and combinations thereof. For instance, organic solvents may be selected from the group consisting of methanol, acetone, and combinations thereof.

Suitable fluid dyestuffs include a water soluble dye, for example, FD&C blue #1, FD&C blue #2, FD&C Green #3, FD&C Red #40, C.I. Food Blue 5, and C.I. Food Red 7, and any combination thereof.

Suitable resins include any water soluble resin, for example, a cellulous derivative, an acrylamide, a polyamide, polyvinyl alcohol, carboxymethoxylcellulous, polyvinylpyrrolidone, and any combination thereof. A preferred water soluble resin is polyvinylpyrrolidone, PVP K-15 available from ISP.

Suitable surfactants include a surfactant selected from the group consisting of cationic surfactant, anionic surfactant, non-inonic surfactant and amphoteric surfactant, and the combination thereof.

Exemplary water soluble ink compositions that can be used in accordance with the present invention are commercially available from Videojet Technologies, Ill., USA, under the trade names "Z6-5236" and "Z6-5307".

In one embodiment, upon contact with an aqueous liquid, the water soluble ink composition of the background graphic dissolves and the central graphic is not affected by the liquid. The central graphic then becomes apparent upon dissolution of the background graphic. The change in visibility of a graphic or a portion of a graphic can be determined based on a person's observation of the graphic before and after the graphic is exposed to liquid.

Backsheet graphics are directly visible on the exterior surface of the absorbent article and have been extremely appealing to children. Moreover, parents and caregivers can use outer cover graphics as educational and motivational tools to advance the toilet training process. Thus, the background and central graphics are suitably disposed on the backsheet. The term "disposed" and variations thereof are intended to mean that one element can be integral with another element, or that one element can be a separate structure bonded to or placed with or placed near another element. Thus, the graphics of the wetness indicator can be formed or applied directly or indirectly to a surface of the backsheet, formed or applied between layers of a multiple layer backsheet, formed or applied to a substrate that is placed with or near the outer cover, formed or applied within a layer of the backsheet or another substrate, or other variations or combinations thereof. In particular embodiments, the graphic can be printed via continuous inkjet printing directly on a layer of the outer cover. In other embodiments, the graphic can be applied to a layer placed with or near the backsheet, such as a substrate associated with the absorbent assembly, including but not limited to tissue layers, liquid handling layers, absorbent layers, and the like.

In one embodiment, the background and central graphics can be printed via continuous inkjet printing, for example, traditional continuous ink jet printing or binary array ink jet printing. Any continuous inkjet printer known in the printer industry which can print graphics based on graphic data stored in a memory device can be used as the printer. An exemplary continuous inkjet printer is available from Videojet Technologies, Ill., USA, under the trade name "PrintPro". In one example, the continuous inkjet printer has a maximum resolution of 128 dpi and a maximum print speed of 975 fpm. As a result, the inkjet printer produces a wetness indicator graphic which can be readily altered without the need to shut down a printing line to change printing plates and the like, thus enabling a manufacturer to vary the graphic produced to suit a purchaser's individual requirements and to switch between one graphic and another at will without having to stop the production line.

In operation, the water soluble ink and permanent ink are applied in sequence. However, the water soluble ink can be applied either before or after the permanent ink. In addition, the water soluble ink and permanent ink can be applied as discrete dots adjacent to each other or the dots can overlap in order to form the wetness indicator graphic. For example, color can be "built" by printing two different color dots adjacent to each other. Built color "purple" can be formed by inkjet printing permanent ink color "red" adjacent to water soluble ink color "blue".

The background graphic may be in liquid communication with the absorbent assembly of the product. As used herein, the term "liquid communication" means that liquid such as urine is able to travel from one layer or element to another layer or element. The absorbent assembly can but need not include a slot or densified region, incorporate a liquid distribution layer, or the like, to channel or direct liquid to the location near the outer cover where the graphics are located.

Absorbent articles suitable for use as the present invention include diaper 20, training pants, incontinence products, diaper pants, disposable underwear, or the like. Suitable training pants and diaper pants can have seamed side portions or refastenable side portions. The present invention is particularly suited for use with training pants or diaper pants to aid in toilet training. Particular diapers and training pants suitable for use with the present invention are disclosed in U.S. Pat. Nos. 3,860,003, 4,636,207, 4,695,278, 4,704,115, 4,795,454, 4,900,317, 4,909,803 (Reissued as USRE34,920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Additional patents discussing suitable training pants are disclosed earlier herein.

In one embodiment, the absorbent article further comprises at least a first cuff for providing improved containment of liquids and other body exudates; an elastic waist feature that provides improved fit and containment; and a fastening system which forms a side closure which maintains the first waist region and the second waist region in an overlapping configuration such that lateral tensions are maintained around the circumference of the absorbent article to maintain the absorbent article on the wearer. The absorbent article may also comprise elasticized side panels 80 in the waist regions and to provide an elastically extensible feature that provides a more comfortable and contouring fit and more effective application of the absorbent article.

The "elasticized" leg cuffs 60 can be constructed in a number of different configurations, including those described in U.S. Pat. Nos. 3,860,003, 4,636,207, 4,695,278, 4,704,115, 4,795,454, 4,900,317, 4,909,803 (Reissued as USRE34,920), U.S. Pat. Nos. 5,085,654, 5,492,751, 6,476,288 and SIR H1630. For example, the absorbent article may include one ore more first cuffs that provide improved containment of liquids and other body exudates. First cuffs may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Additionally, an absorbent article of the present invention may include one or more second cuffs that also provide improved containment of liquids and other body exudates. Second cuffs may also be referred to as barrier leg cuffs 60, inner leg cuffs or "stand-up" elasticized flaps. U.S. Pat. Nos. 4,808,178 and 4,909,803 (Reissued as USRE34,920), respectively, describe disposable diapers having "stand-up" elasticized flaps that improve the containment of the leg regions.

First cuff and second cuff may both be provided by way of a dual cuff, as exampled in U.S. Pat. Nos. 4,695,278 and 4,795,454. Additional cuffs may be provided in an article of the present invention as detailed in US Statutory Invention Registration H1630.

Another component that may be included in the articles or composites of the present invention is a hydrophobic surface coating as disclosed in copending U.S. application Ser. No. 11/055,743 filed on Feb. 10, 2005 in the name of K. Catalan. (P&G Case 9528M). This hydrophobic surface coating may be paired with the barrier coating of the present invention on the barrier layer or may be disposed adjacent to one or more additional components of the absorbent articles or composites of the present invention. For instance, this hydrophobic surface coating may be disposed on an interior surface of one or more leg cuffs, waist portions, or other areas of the absorbent article.

EXAMPLES

The following examples are given solely for the purpose of illustration and are not to be construed as limitations of the present invention, as many variations of the invention are possible without departing from the spirit and scope of the invention.

Example 1

An absorbent article that includes a wetness indicator according to the present invention is produced as follows. A non-breathable polyolefin film is selected from either of DH-279 or BR-120, which are commercially available from Clopay of Cincinnati, Ohio. DH-279 has a basis weight of 14 gsm, while BR-120 has a breathability of 1500 MVTR and basis weight of 28 gsm. Either of these films may serve as the material on which printing occurs. A two head continuous ink jet printer available from Videojet Technologies, Ill., USA, under the trade name "PrintPro" is used to print the wetness indicator. One print head is loaded with permanent ink (color red) and a second print head is loaded with a water soluble ink (color blue). The permanent ink is available from Videojet Technologies, Ill., USA, under the trade name "16-71". The water soluble ink is available from Videojet Technologies, Ill., USA, under the trade name "Z6-5236". The film is printed first with the permanent ink (central graphic), followed by the water soluble ink (background graphic), at a print speed of 900 fpm and a maximum resolution of 128 dpi. A purple colored graphic appears.

This film is then dried at ambient temperature and wound on to a roll and stored. The film is then converted into a diaper. Next, the film is tested with 70 ml warm (35±° C.) saline solution. Within approximately 30 seconds of wetting the film, the blue water soluble ink in the background graphic starts to dissipate and leaves a red colored central graphic on the film.

Example 2

An absorbent article that includes a wetness indicator according to the present invention is produced as follows. A non-breathable polyolefin film is selected from either of DH-279 or BR-120, which are commercially available from Clopay of Cincinnati, Ohio. DH-279 has a basis weight of 14 gsm, while BR-120 has a breathability of 1500 MVTR and basis weight of 28 gsm. Either of these films may serve as the material on which printing occurs. A two head continuous ink jet printer available from Videojet Technologies, Ill., USA, under the trade name "PrintPro" is used to print the wetness indicator. One print head is loaded with permanent ink (color red) and a second print head is loaded with a water soluble ink (color blue). The permanent ink is available from Videojet Technologies, Ill., USA, under the trade name "16-71". The water soluble ink is available from Videojet Technologies, Ill., USA, under the trade name "Z6-5236". The film is printed first with the permanent ink (central graphic), followed by the water soluble ink (background graphic), at a print speed of 900 fpm and a maximum resolution of 128 dpi. A purple colored graphic appears.

This film is then dried at ambient temperature and wound on to a roll and stored. The film is then converted into a diaper. Next, the film is tested with 70 ml warm (35±° C.) saline solution. Within approximately 30 seconds of wetting the film, the blue water soluble ink in the background graphic starts to dissipate and leaves a red colored central graphic on the film. As indicated in FIG. 3, the background graphic that appears prior to wetting may differ from the central graphic that appears afterwards.

Example 3

An absorbent article that includes a wetness indicator according to the present invention is produced as follows. A non-breathable polyolefin film, DH-279, serves as the material on which printing occurs. DH-279 is commercially available from Clopay of Cincinnati, Ohio and has a basis weight of 14 gsm. A two head continuous ink jet printer available from Videojet Technologies, Ill., USA, under the trade name "PrintPro" is used to print the wetness indicator. One print head is loaded with permanent ink (color blue) and a second print head is loaded with a water soluble ink (color blue). The permanent ink is available from Videojet Technologies, Ill., USA, under the trade name "16-44". The water soluble ink is available from Videojet Technologies, Ill., USA, under the trade name "Z6-5236". The film is printed first with the permanent ink (central graphic), followed by the water soluble ink (background graphic), at a print speed of 900 fpm and a maximum resolution of 128 dpi. A blue colored graphic appears.

This film is then dried at ambient temperature and wound on to a roll and stored. The film is then converted into a diaper. Next, the film is tested with 70 ml warm (35±° C.) saline solution. Within approximately 30 seconds of wetting the film, the blue water soluble ink in the background graphic starts to dissipate and leaves a blue colored central graphic on the film. As indicated in FIG. 3, the background graphic that appears prior to wetting may differ from the central graphic that appears afterwards.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a) a body contacting surface;
b) a garment contacting surface opposite the body contacting surface; and
c) an inkjet printed wetness indicator which is seen through either the body contacting surface or the garment contacting surface; the wetness indicator comprising a permanent hidden central graphic and a water soluble background graphic, wherein the hidden central graphic having at least one permanent ink composition and the background graphic having at least one water soluble ink composition, the central graphic and the background graphic together comprising inkjet-applied dots of the permanent ink composition that are adjacent or overlapping inkjet-applied dots of the water soluble ink composition, such that upon wetting, the background graphic exhibits a visible change resulting in the hidden central graphic being revealed, wherein the visible change is selected from the group consisting of a color change, a graphic change, and combinations thereof; and wherein the revealed hidden central graphic is visible through either the body contacting surface or the garment contacting surface; and
wherein the inkjet-applied dots of the permanent ink composition have a first color, the inkjet-applied dots of the water soluble ink composition have a second color, and the respective dots are disposed adjacent each other to form a built third color.

2. The article of claim 1, further comprising a component material disposed between the body contacting surface and the garment contacting surface.

3. The article of claim 2, wherein the component material is selected from the group consisting of a backsheet, a topsheet, an acquisition layer, an absorbent core, leg cuffs, and combinations thereof.

4. The article of claim 3, wherein the backsheet is either breathable or non-breathable.

5. The article of claim 1, wherein the water soluble ink composition comprises:

a) from about 1% to about 10%, by weight of the composition, of a fluid dyestuff;
b) from about 1% to about 10%, by weight of the composition, of a resin;
c) from about 1% to about 10%, by weight of the composition, of a plasticizer; and
d) from about 50% to about 90%, by weight of the composition, of a solvent.

6. The article of claim 5, wherein the solvent is an organic solvent.

7. The article of claim 6, wherein the organic solvent is selected from the group consisting of methanol, acetone, and combinations thereof 8. The article of claim 1, wherein the wetness indicator is printed via continuous inkjet printing.

9. A disposable absorbent article comprising:
a) a liquid pervious topsheet;
b) a liquid impervious backsheet that is at least partially joined to the topsheet;
c) an absorbent core disposed at least partially between the topsheet and the backsheet; and
d) a wetness indicator inkjet printed onto a surface of either the absorbent core or the backsheet, the wetness indicator having a permanent hidden central graphic and a water soluble background graphic, wherein the hidden central graphic includes at least one permanent ink composition and the background graphic includes at least one water soluble ink composition, the central graphic and the background graphic together comprising inkjet-applied dots of the permanent ink composition that are adjacent or overlapping inkjet-applied dots of the water soluble ink composition, such that upon wetting, the background graphic exhibits a visible change resulting in the hidden central graphic being revealed, wherein the visible change is selected from the group consisting of a color change, a graphic change, and combinations thereof; and wherein the revealed hidden central graphic is visible through either the liquid pervious topsheet or the liquid impervious backsheet; and
wherein the inkjet-applied dots of the permanent ink composition have a first color, the inkjet-applied dots of the water soluble ink composition have a second color, and the respective dots are disposed adjacent each other to form a built third color.

10. The article of claim 9, wherein the wetness indicator is in liquid communication with the absorbent core.

11. The article of claim 9, wherein the wetness indicator is printed via continuous inkjet printing.

12. A method of printing a wetness indicator onto an absorbent article, the method comprising the steps of:
a) providing an absorbent article wherein said article comprises a liquid pervious topsheet, a liquid impervious backsheet and an absorbent core; and
b) inkjet printing a wetness indicator onto a surface of the absorbent article, the wetness indicator having a permanent hidden central graphic and a water soluble background graphic, wherein the hidden central graphic includes at least one permanent ink composition and the background graphic includes at least one water soluble ink composition, the central graphic and the background graphic together comprising inkjet-applied dots of the permanent ink composition that are adjacent or overlapping inkjet-applied dots of the water soluble ink composition, such that upon wetting, the background graphic exhibits a visible change resulting in the hidden central graphic being revealed, wherein the visible change is selected from the group consisting of a color change, a graphic change, and combinations thereof; and wherein the revealed hidden central graphic is visible through either the liquid pervious topsheet or the liquid impervious backsheet;and
wherein the inkjet-applied dots of the permanent ink composition have a first color, the inkjet-applied dots of the water soluble ink composition have a second color, and the respective dots are disposed adjacent each other to form a built third color.

13. The method of claim 12, wherein the backsheet is either breathable or non-breathable.

14. The method of claim 12, wherein the water soluble ink composition comprises:
a) from about 1% to about 10%, by weight of the composition, of a fluid dyestuff;
b) from about 1% to about 10%, by weight of the composition, of a resin;
c) from about 1% to about 10%, by weight of the composition, of a plasticizer; and
d) from about 50% to about 90%, by weight of the composition, of a solvent.

15. The method of claim 14, wherein the solvent is an organic solvent.

16. The method of claim 12, wherein the wetness indicator is printed via continuous inkjet printing.

17. The method of claim 16, wherein the continuous inkjet printing is binary array printing.

* * * * *